United States Patent [19]

Husain

[11] Patent Number: 5,801,809
[45] Date of Patent: Sep. 1, 1998

[54] EYE CHART WITH COLOR VISION SCREENING

[76] Inventor: Abbas M. Husain, 8 Bunning Dr., Voorhees, N.J. 08043

[21] Appl. No.: 743,701

[22] Filed: Nov. 6, 1996

[51] Int. Cl.⁶ .................................................. A61B 3/02
[52] U.S. Cl. ............................................. 351/239; 351/237
[58] Field of Search ................................. 351/239, 237, 351/246, 242, 241, 240

[56] References Cited

U.S. PATENT DOCUMENTS 1,412,902  4/1922  Tallman .
2,184,929  12/1939  Bigelow .
2,190,008  2/1940  Beitel .
2,200,595  5/1940  Diggins .

*Primary Examiner*—Hung Xuan Dang
*Attorney, Agent, or Firm*—Robert D. Thompson, Esquire

[57] ABSTRACT

The present invention is an improvement over existing methods of testing a patient for color perception. The present invention provides a means by which color perception can be tested at the same time that visual acuity is measured. The eye chart with color vision screening comprises a chart which displays objects of progressively smaller sizes with the larger sized objects being displayed in color in order that color perception can be measured and with the smaller objects displayed black on the white background in order that the chart's effectiveness as a tool for measuring visual acuity is not reduced.

6 Claims, 1 Drawing Sheet

EYE CHART WITH COLOR VISION SCREENING

BACKGROUND OF INVENTION

Screening of visual acuity is conventionally done with the use of an "eye chart" that is comprised of a series of letters of progressively smaller sizes. The patient is asked to read down the chart until the letters become too small for the patient to distinguish. The last line of letters that can be correctly read defines that patient's limit of visual acuity. In order to provide the best viewing conditions for this evaluation, eye charts are typically printed with black block letters on a bright white background.

Color perception is conventionally tested with the use of a set of special plates that have numbers or patterns printed in subtle color patterns that will become invisible if the patient has specific types of color vision impairment. One such method is the one developed by Dr. Shinobu Ishihara of the University of Tokyo. While these methods are accurate, they are expensive and time consuming for the doctor to perform. For a general screening of color vision, the much simpler method as disclosed by this invention is sufficient.

It is an objective of this invention to provide a single type of eye chart which can be used to simultaneously evaluate visual acuity and color perception.

CROSS-REFERENCES TO RELATED APPLICATIONS

None.

SUMMARY OF INVENTION

This invention is an improvement to the conventional eye chart used by an examining physician to measure visual acuity. Through the addition of colors to the conventional eye chart, the examining physician can determine the patient's ability to perceive typical colors encountered in normal daily activity. As the patient reads the eye chart, the patient is asked to call out the color as well as identify the object on the chart. While the larger, more easily perceived objects on the eye chart are displayed in different colors, the smaller objects remain displayed in black type on a white background so as not to impair the use of the chart to measure visual acuity while also providing a means for defining the ability to perceive different colors.

DETAILED DESCRIPTION

Figure 1:
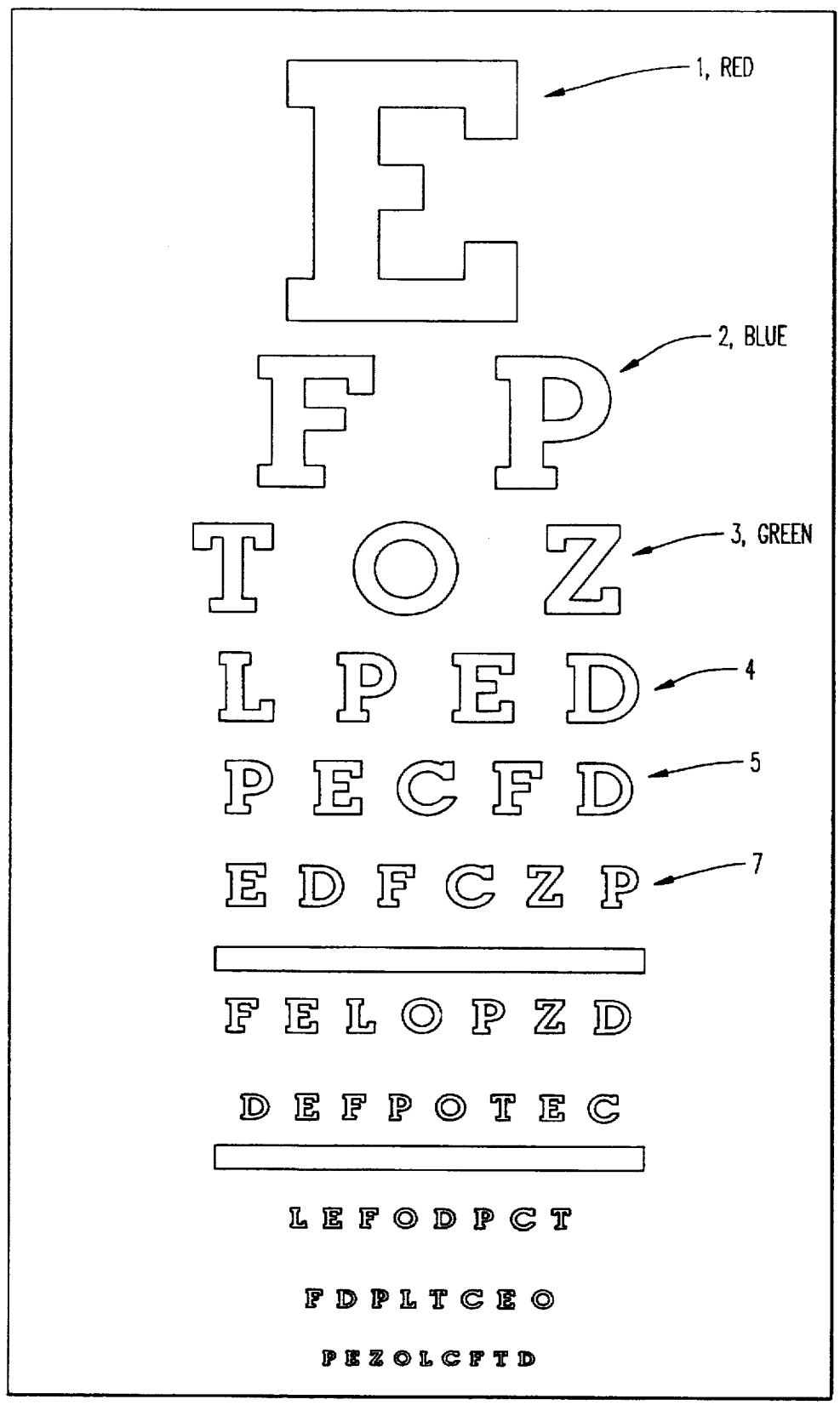
FIG. 1 is a drawing of an eye chart showing the features of this invention.

Referring to FIG. 1, an eye chart of conventional design is shown, containing letters of decreasing size as the chart is read downward. The patient is directed to read across and down the chart until the patient can no longer correctly identify the letters. This point is the limit of the patient's acuity of vision. The larger letters, 1, 2 and 3, are displayed in the primary colors, red, blue and green, as indicated by the legends in FIG. 1. Lines 3, 4 and 6 are displayed with each letter in a different color. The patient is asked to call out the color of each letter as it is read. This tests the patient's ability to distinguish specific colors. For example, the colors in lines 4, 5 and 6 might be:

| | | | | | | |
|---|---|---|---|---|---|---|
| Line 4 | L<br>Purple | P<br>Red | E<br>Lt. Blue | D<br>Yellow | | |
| Line 5 | P<br>Green | E<br>Orange | C<br>Purple | F<br>Blue | D<br>Red | |
| Line 6 | E<br>Blue | D<br>Yellow | F<br>Green | C<br>Orange | Z<br>Lt. Blue | P<br>Purple |

Because of the eye's poorer acuity for colors, the remaining lines of the eye chart are displayed in black. Thus, the color testing does not interfere with the normal testing of acuity.

Although this invention has been disclosed and illustrated with reference to a particular embodiment, the principles involved are susceptible for use in numerous other embodiments which will become apparent to a person skilled in the art.

What is claimed is:

1. An eye chart for the measurement of visual acuity comprised of objects of multiple colors and decreasing sizes wherein the improvement comprises the use of colored objects of decreasing sizes to test color perception and visual acuity simultaneously.

2. The device as set forth in claim 1 above, wherein, of the objects of multiple colors and decreasing sizes, only the larger objects are colored while the smaller objects remain black on white in order to provide simultaneous color and visual acuity testing while maintaining the effectiveness of the eye chart as a measurement for visual acuity.

3. The device as set forth in claim 2 above, said objects being letters of progressively smaller sizes.

4. The device as set forth in claim 1 above, said objects being letters of decreasing sizes.

5. In combination for the simultaneous testing of visual acuity and color perception, a pattern comprising a series of objects displayed progressively from larder to smaller sizes, the larger sizes of said objects displayed in different colors.

6. In combination for the simultaneous testing of visual acuity and color perception, a pattern comprising a series of letters displayed progressively from larger sizes to smaller sizes, the larger sizes of said letters displayed in different colors.

* * * * *